United States Patent [19]
Hundertmark et al.

[11] Patent Number: 5,895,402
[45] Date of Patent: Apr. 20, 1999

[54] INTRAVASCULAR CATHETER WITH GUIDING STRUCTURE

[76] Inventors: Ron Ray Hundertmark, San Mateo; Brian Farley, Los Altos; Kent D. Dell, Redwood City; Bernard H. Andreas, Fremont, all of Calif.

[21] Appl. No.: 08/784,404

[22] Filed: Jan. 17, 1997

Related U.S. Application Data

[63] Continuation of application No. 08/357,999, Dec. 16, 1994, Pat. No. 5,643,296.

[51] Int. Cl.[6] .................................................. A61B 17/32
[52] U.S. Cl. .......................... 606/171; 606/170; 606/159; 604/93; 604/96
[58] Field of Search .............................. 604/95, 22, 52, 604/53, 93, 96, 171; 600/104; 606/159, 170, 180, 171

[56] References Cited

U.S. PATENT DOCUMENTS

| | | |
|---|---|---|
| Re. 33,569 | 4/1991 | Gifford, III et al. . |
| 4,669,469 | 6/1987 | Gifford, III et al. . |
| 4,771,774 | 9/1988 | Simpson et al. . |
| 4,781,186 | 11/1988 | Simpson et al. . |
| 4,926,858 | 5/1990 | Gifford, III et al. . |
| 4,979,951 | 12/1990 | Simpson . |
| 5,047,040 | 9/1991 | Simpson . |
| 5,078,722 | 1/1992 | Stevens . |
| 5,084,010 | 1/1992 | Plaia et al. . |
| 5,226,909 | 7/1993 | Evans et al. . |
| 5,250,059 | 10/1993 | Andreas et al. . |
| 5,269,793 | 12/1993 | Simpson . |
| 5,441,510 | 8/1995 | Simpson et al. . |
| 5,624,457 | 4/1997 | Farley et al. .............. 606/170 |

*Primary Examiner*—Wynn Wood Coggins
*Assistant Examiner*—N. Kent Gring

[57] ABSTRACT

Intravascular catheters that include a flexible catheter body, a distal housing secured to the catheter body, a work element disposed within the housing and exposed to the external environment through a side window, and a guiding structure for the work element, are disclosed. An axial path through the housing is defined by the guiding structure. Embodiments of the guiding structure include a slot or channel formed in the housing, a coaxial tube attached to the housing, a radially offset ribbon attached to the housing, or the external surface of the housing itself. The work element, such as a rotatable cutting blade in an atherectomy catheter, is coupled to the guiding structure such that the work element is retained within the housing during insertion and operation of the catheter and even when the housing is bent or distorted as a result of bends in the blood vessel.

27 Claims, 7 Drawing Sheets

INTRAVASCULAR CATHETER WITH GUIDING STRUCTURE

This is a continuation of application Ser. No. 08/357,999 filed on Dec. 16, 1994, now U.S. Pat. No. 5,643,296.

BACKGROUND OF THE INVENTION

1. Field of the Invention

The present invention generally relates to the construction and use of vascular catheters. More particularly, the invention relates to intravascular catheters having a work element within a distal housing, and a work element guiding structure.

2. Previous Art

Arteriosclerosis, also known as atherosclerosis, is a disease characterized by the deposition of a fat-like substances, referred to as atheroma or plaque, on the walls of blood vessels. Such deposits can occur both in peripheral blood vessels that feed the limbs of the body and in coronary blood vessels that feed the heart. When deposits accumulate in localized regions of a blood vessel, the regions become "stenosed;" blood flow is restricted and the person's health is at serious risk.

Numerous approaches for restoring blood flow by reducing and removing stenotic deposits have been proposed. Balloon angioplasty, for example, uses a balloon-tipped catheter to dilate the stenosed region. Atherectomy procedures use a blade or other cutting element to sever and remove stenotic material. Laser angioplasty directs laser energy to ablate at least a portion of the stenotic material.

Of particular interest are atherectomy catheters in which a cutting blade advances past an opening at the distal end of a vascular catheter. The catheter exposes the opening to at least a portion of the stenotic material. The stenotic material extends through the opening where the cutting blade advances and severs the stenotic material. Typically, such cutting blades are circular and are rotated (or rotationally oscillated) and advanced simultaneously to effect the desired cutting.

Although such atherectomy catheters have enjoyed widespread success in both peripheral and coronary applications, certain design limitations persist. In small diameter catheters used in the coronary arteries, for example, very tight vascular bends are encountered. Typically, a guidewire is first inserted through the blood vessel and advanced along the lumen of the vessel until proximate to the stenosed region. The catheter slides over, and along, the guidewire until the catheter positions adjacent a stensosed region. Atherectomy catheters having rigid housings at their distal ends have difficulty inserting past tight vascular bends. The rigidity of the housing causes lateral displacement of the guidewire. Difficulties associated with guide wire movement and tight vascular bends are exacerbated by elongated housings which frequently collect severed stenotic material in a forward nosecone.

In an effort to enhance the maneuverability within the tortuous regions of the coronary arteries, atherectomy catheters having flexible cutter housings have been employed. Commonly assigned flexible housings take various forms, including a braid-reinforced polymeric structure and a slotted metal tubular structure.

Although flexible housings offer a significant improvement over comparably sized rigid cutter housings when employed in coronary arteries and other tortuous regions of the vascular system, they do present limitations. In particular, bending and flexing of the flexible housings inhibits the axial advancement of the cutting blades within the housing. Also, bending of the housing sometimes causes an advancing cutting blade to undesirably extend outward from the window. Outward extension of the cutting blade may render the cutting blade inoperable or interfere the housing and the guidewire. Such consequences prevent proper operation of the catheter by distorting the housing. Outwardly extending cutting blades are unwieldy and generally undesirable.

Efforts to overcome undesired extension of cutting blades continue. Reducing the width of the housing window prevents extension of the cutting blades. This modification, however, reduces the amount of stenotic material which can be removed in a single pass of the cutting blade through the housing.

Various related efforts manifest themselves in atherectomy catheters described in U.S. Pat. No. 4,926,858, issued May 22, 1990 to Gifford, III et al. entitled "ATHERECTOMY DEVICE FOR SEVERE OCCLUSIONS"; U.S. Pat. No. 4,979,951, issued Dec. 25, 1990, to Simpson, entitled "ATHERECTOMY DEVICE AND METHOD"; U.S. Pat. No. 5,047,040, issued Sep. 10, 1991, to Simpson et al. entitled "ATHERECTOMY DEVICE AND METHOD"; U.S. Pat. No. 5,084,010, issued Jan. 28, 1992, to Plaia et al., entitled "SYSTEM AND METHOD FOR CATHETER CONSTRUCTION"; and Re. 33,569, issued Apr. 9, 1991, to Gifford III et al. entitled "SINGLE LUMEN ATHERECTOMY CATHETER DEVICE". Of these, the 4,979,951 and Re. 33,569 patents describe catheters having distal housings in which a rotatable cutting blade receives a coaxial movable guidewire. Moveable guidewires generally do not securely hold the cutting blade within the housing. Additionally, in some devices, the guidewire itself may be severed by the cutting blade. Copending, U.S. Pat. No. 5,250,059, issued Oct. 5, 1993 to Andreas et al., entitled "ATHERECTOMY CATHETER HAVING FLEXIBLE NOSE CONE", application, and describes an atherectomy catheter having a flexible nose cone attached to the distal end of a cutter housing. A rotatable cutting blade is optionally received over a movable guidewire which passes through the nose cone, the housing and the cutting blade drive (torque) cable.

Placement of the cutting blade of an atherectomy catheter over a conventional movable guidewire has been proposed (See, U.S. Pat. Nos. 4,669,469, and Re. 33,569). Conventional guidewires could restrain the cutting blade within the cutter housing under some circumstances. Unfortunately, the guidewire itself will often be displaced as the atherectomy catheter is advanced over the guidewire.

Guidewire movement is due to the fine gauge (usually 0.007 inch) of the guide wire. Furthermore, since the guidewire is not fixed at its distal end, it does not necessarily conform to the specific distortions of the housing within a contorted blood vessel, and thus is not always efficient in guiding the cutter as it is advanced within the housing. Thus, movable guidewires cannot be relied on to cooperate with an axially translatable cutter within the cutter housing under all circumstances.

Improved intravascular catheters are desired. In particular, it is desirable to provide a way of retaining a cutting blade (work element) within the housing of a catheter. It is desirable to provide a housing in which the cutting blade will not interfere with the guidewire or the housing of the catheter. It is desirable to provide a way of retaining the cutting blade which is compatible with housings of various sizes and configurations.

SUMMARY AND OBJECTS OF THE INVENTION

The various objects of the invention which are presented and which will become apparent below are presented by way of example only and are not intended to limit the scope of the present invention. The present invention is to be limited only by the Claims.

It is an object of this invention to provide intravascular catheters suitable for operation in blood vessels with tight bends.

It is a further object of this invention to provide intravascular catheters with work elements that are retained within flexible distal housings during insertion and operation of the catheter.

It is a further object of this invention to provide intravascular catheters with a work element that follows the longitudinal path of the housing during axially translation of the work element.

It is a further object of this invention to provide methods of using intravascular catheters with guiding structures in intravascular surgical interventions.

It is a further object of this invention to provide methods of using atherectomy catheters with guiding structures to perform coronary atherectomies.

In accordance with the above objects and those that will be mentioned and will become apparent below, the intravascular catheter of the present invention comprises:

- a catheter body having a proximal end, a distal end and a lumen therebetween;
- a housing with a cylindrical body, a longitudinal axis, an internal surface, an external surface, a window on a lateral side thereof, and an open proximal end secured to the distal end of the catheter body, the housing defining a hollow interior;
- a work element disposed within the housing and having a proximal end;
- a cable substantially disposed within the lumen of the catheter body, the connector having a proximal end and a distal end and the distal end being connected to the proximal end of the work element;
- a guiding structure affixed to the housing and slidably connected to the work element, the guiding structure defining a fixed axial path relative to the housing,
- whereby the work element is retained within the housing during insertion of the catheter within a blood vessel and during axial translation of the work element along the axial path of the guiding structure.

The catheters of the embodiments of the present invention all include a guiding structure affixed to or incorporated into the housing and slidably connected to the work element. The catheters also have other additional features in common. These include a long flexible catheter body with a housing attached to the distal end. The housing has an opening along a lateral side. The work element is disposed within the housing. A cable is attached to the work element. The connector goes from the work element, through the catheter body and out its proximal end. The work element within the housing is operated from the proximal end of the catheter body via the cable.

In an embodiment of the invention, the guiding member includes at least two longitudinal slots through the internal surface of the housing. A slider is attached to the work element and has pins projecting radially that are positioned within each slot and able to slide along the slot as the work element is moved back and forth. The angle between the pins insures that the pins remain in their slots and this insures that the work element stays within the housing and follows the axial path of the housing even when the housing is bent.

In another embodiment, a single longitudinal slot is provided along the housing. This slot is substantially a tunnel within the body of the housing and communicates with the hollow interior of the housing through a narrow axial neck. A slidable pin conforming to the shape of the slot is positioned within the slot and attached to a slider which in turn is attached to the work element, thereby registering the axial path of the work element to the housing.

In an additional embodiment, the guiding member is a longitudinal shaft, sometimes tubular and sometimes ribbon shaped, usually flexible. The shaft is positioned within the hollow interior of the housing and attached to the housing. The shaft passes through a tunnel attached to or within the work element such that the work element is slidable along the shaft.

In a particular configuration of this embodiment, the shaft is coaxial with the longitudinal axis of the housing and the tunnel is in the center of the work element, permitting the work element to rotate about the shaft.

In yet another embodiment, the guiding member includes the exterior surface of the housing, and a band is coupled to the work element and circumscribes the exterior surface of the housing. The band slides alone with the work element and keeps the work element inside of the housing.

According to an embodiment of the method of the present invention, an intravascular catheter as described herein is provided. The catheter is inserted into the lumen of a blood vessel starting from the distal end of the catheter. The catheter is advanced until the housing is adjacent to a site of interest, e.g. stenotic material within a blood vessel. The work element is then operated in a manner specific to the function of the work element. The path of axial movement of the work element within the housing is registered to the axial path provided by the guiding member.

The intravascular catheter of the present invention can be fitted with a variety of work elements each performing a specific task. The cable is chosen to complement the function of the work element. For example, when the work element is a cutting blade, the cable is rotated which in turn rotates, the cutting blade, the cable is translated to axially to advance the cutting blade past the lateral window of the housing, whereby stenotic material extending through the window into the hollow interior of the housing is severed.

It is to be understood that the intravascular catheter of the present invention is conceived to operate with a variety of work elements and corresponding connectors that differ in the interventional task that each is designed to perform. A wide variety of work elements (and cables) are known to those skilled in the art, e.g. cutting blades (and cables) for performing atherectomy procedures, heated elements (electrical wires) for performing thermal ablation, electrodes (electrical wires) for performing electrosurgical cutting and cauterization, abrasive elements for performing mechanical ablation (cables), optical waveguides (fiber optic lines) for performing laser ablation, ultrasonic transducers (ultrasonic transduction lines) for imaging and ablation, angioscopic imaging devices (fiber optic lines) and the like. The present invention is particularly useful for work elements requiring axial translation during operation.

It is an advantage of the intravascular catheters of the instant invention to be operable in blood vessels with tight bends, e.g. coronary arteries.

It is a further advantage of the catheters of this invention to be compatible with flexible housings and to be operable when the housing is bent or distorted.

It is an additional advantage of the catheters of this invention to have work elements whose axial translational path is registered to the axial path within the housing.

It is a further advantage of the catheters of this invention that escape of the work element through the window on a lateral side of the housing is minimized.

It is yet another advantage of this invention to be able to use housings with wide windows while retaining the work element within the housing.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 1:
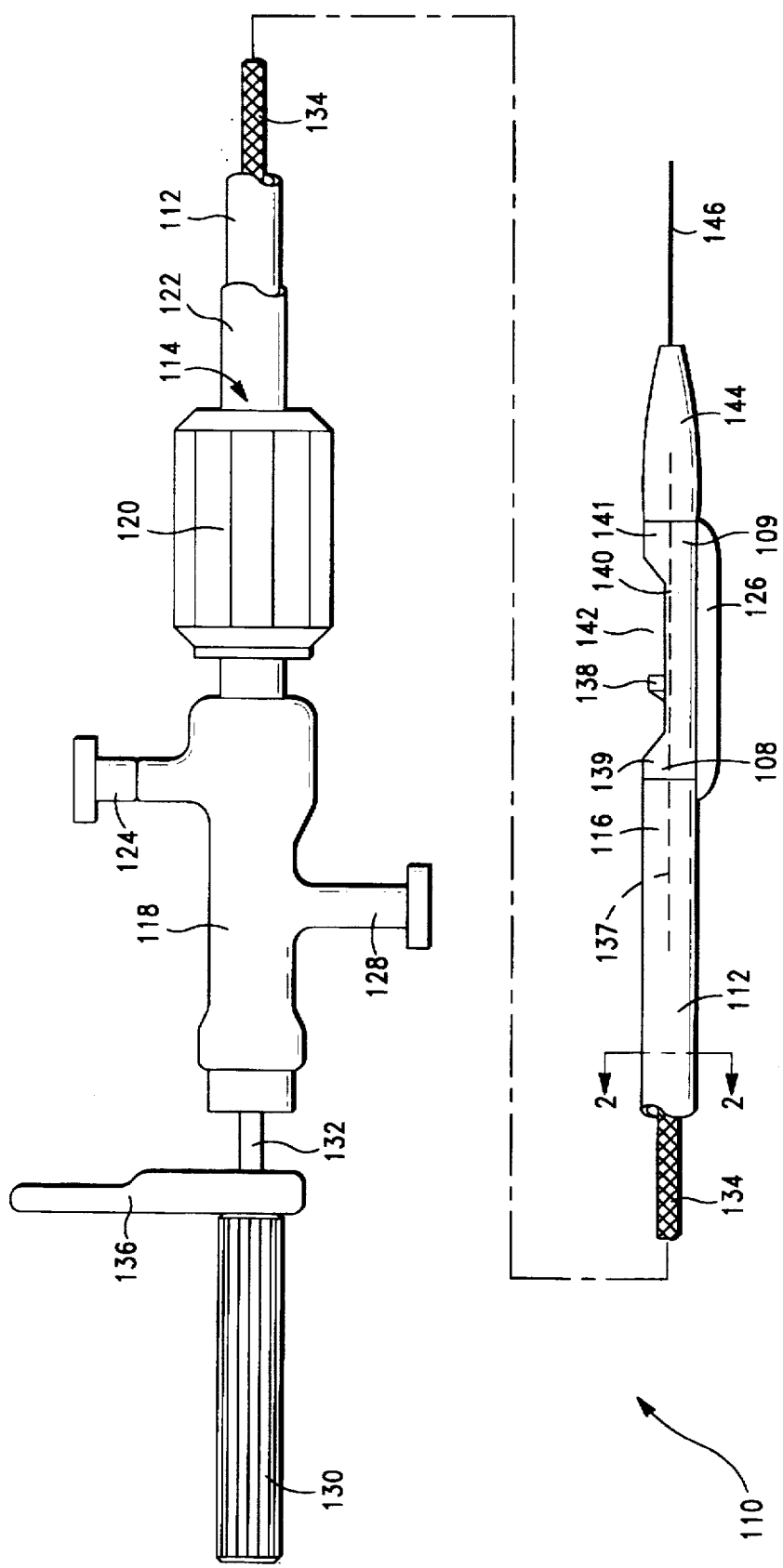
FIG. 1 is a side elevational view of an intravascular atherectomy catheter with the work Guiding structure of the present invention.

The present invention provides intravascular catheters with guiding structures 100. The catheters include an elongated flexible catheter body and a housing secured to the distal end of the catheter body. The housing holds the work element adjacent to an elongated window. The window is located on a lateral side of the housing. A cable extends through a lumen of the catheter body and attaches to the work element. The cable operates the work element within the housing.

The invention features guidance and retention structures for the work element within the housing. Particularly, the invention provides a guiding member that retains the work element within the housing, prevents escape of the work element through the window of the housing, and guides the axial translation of the work element along the longitudinal axis of the housing. The work element is thus contained when very wide windows are provided in the housing or when the housing is flexible and subjected to bending, deformation or distortion which might otherwise cause the work element to be lost from the housing.

The present invention is useful with a wide variety of catheters having virtually any type of axially translatable work element. The present invention is especially useful in atherectomy applications where the work element is a rotating or rotationally oscillating cutting blade and is operated by simultaneously rotating and axially advancing the blade past the side window in the housing in order to sever and remove stenotic material from an area of interest, e.g. a stenosed region of blood vessel. Such atherectomy devices and procedures are described in U.S. Pat. Nos. 4,669,469; 4,926,858; 4,979,951; 5,047,040; 5,084,010; and Re. 33,569, the full disclosures of which are incorporated herein by reference.

Preferred embodiments of the present invention are catheters particularly adapted to perform atherectomies. Consequently, in several embodiments the work element is referred to as a "cutting blade" and the cable is referred to as a "cable". It is to be understood, however, that the work guiding structure 100s of the present invention can be used with many other catheter types, all of which are within the intended scope of this invention.

Referring now to the drawings, a number of exemplary embodiments of catheters employing work element guide systems constructed in accordance with the principles of the present invention will be described. It will be appreciated, however, that these embodiments are merely exemplary and that a wide variety of other specific implementations are within the scope of the present invention.

Figure 2:
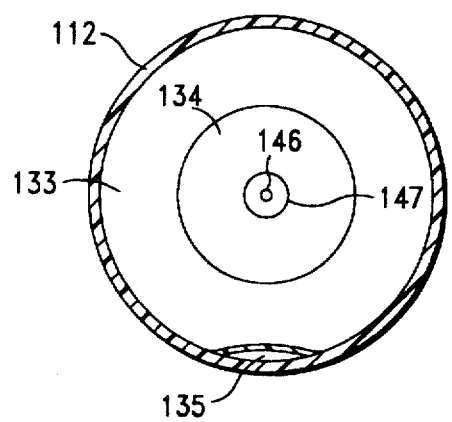
FIG. 2 is a cross-sectional view along line 2—2 of FIG. 1 looking in the direction of the arrows.

Referring now to FIGS. 1 and 2, FIG. 1 shows a side view of an intravascular catheter generally indicated by the reference numeral 110. FIG. 2 a is cross-sectional view of the catheter body 112 of FIG. 1 as seen along the line 2—2 in the direction of the arrows. The catheter body 112 includes a housing 140 with a window 142, a work element 138, and a cable 134.

With particular reference to FIG. 1, there is shown the catheter body 112 which has a proximal end 114, a distal end 116 and at least one internal lumen 133 (FIG. 2). The housing 140 includes a distal end 141 and a proximal end 139. A hollow nose cone 144 attaches to and covers the distal end 141 of the housing 140. The distal end 116 of the catheter body 112 attaches to the proximal end 139 of the housing 140. The lumen 133 of the catheter body 112 holds the cable 134.

The housing 140 is a hollow cylinder having an axis 137, an inner surface 108, an outer surface 109, and a window 142. The proximal end 139 and distal end 141 of the housing 140 are open to establish communication between the catheter body 112 and the nose cone 144.

A balloon 126 attaches on the outer surface 109 of the housing 140 on the side opposite from the window 142. The balloon 126 communicates with a balloon inflation lumen 135 within the catheter body 112 ( FIG. 2). The balloon is inflated when the catheter 110 is positioned within a blood vessel. When the balloon 126 inflates, the balloon 126 pushes the window 142 of the housing 140 against the internal wall of the blood vessel. Atheroma, for example, are invaginated by the window 142 in this way (see FIGS. 11 and 12).

The work element 138 aligns adjacent the window 142. When the window 142 invaginates atheroma, the work element 138 slides within the housing 140 and rotates to cut small pieces of the atheroma. Actuation of the cable 134 rotates and axially translates the work element 138 during operation.

An inflation manifold 118 secures a rotator assembly 120 to the proximal end 114 of the catheter body 112. The rotator assembly 120 permits the catheter body 112 to rotate relative to the inflation manifold 118. A transition element 122 forms over the proximal end 114 of the catheter body 112 and relieves stress between the catheter body 112 and the inflation manifold 118. A fitting 124 on the inflation manifold 118 connects in fluid communication with the with balloon inflation lumen 135 in the catheter body 112. A connector 128 on the inflation manifold 118 interconnects a perfusion or aspiration source in fluid communication with a perfusion lumen of the catheter body 112.

A spline 130 suitable for connection to a motor drive unit (such as that disclosed in U.S. Pat. No. 4,771,774, the disclosure of which is incorporated herein by reference) is secured to a drive shaft 132. The drive shaft 132 connects to the cable 134. The cable 134 extends through the lumen 133 which extends the entire length of the catheter body 112. The cable 134 rotates the work element 138 during operation. An axial advance lever 136 mounts on the drive shaft 132. The lever 136 permits manual axial translation of the cable 134 and work element 138.

A guidewire 146 positions the catheter 110 into an intravascular location, for example. Typically, the guidewire 146 first inserts into a blood vessel. The catheter 110 inserts over the guidewire 146. The guidewire 146 precisely guides the catheter into a desired position within the vascular system of a patient. A lumen 147 in the cable 134 and the nose cone 144 provides a path for the guidewire along the longitudinal axis 137 of the housing 140. The guidewire 146 also passes through a lumen (not shown) in the work element 138.

Referring now to FIGS. 3 through 7, a preferred embodiment of the intravascular catheter of the present invention is shown having a work element 138 and a guiding structure 100. For purposes of the present invention, the work element 138 includes an arcuate cutting edge, for example.

Figure 3:
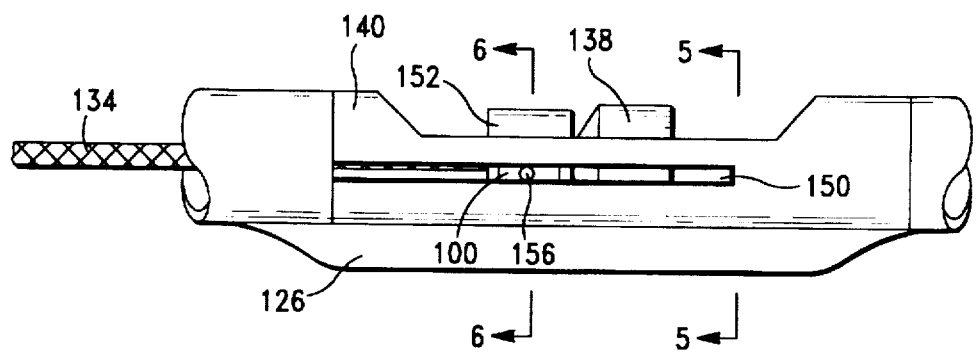
FIG. 3 is a detailed side view of an atherectomy cutter housing.

As seen in FIG. 3, the invention includes a housing 140 with slots 150, a slider 152 with at least one pin 156, a work element 138, and a cable 134. It will be appreciated that the pin 156 could also be formed in the shape of a spline. The slots 150 align inside the housing 140 in parallel with the longitudinal axis 137 (FIG. 1). The slots 150 extend through the housing 140. It should be noted that the slots 150 may extend only partially through the housing 140. The slots 150 receive the pins 156. The pins 156 slide within the slots 150. In the embodiment illustrated in FIG. 3, two slots 150 are shown, however it is to be understood that one or more slots 150 and a corresponding number of pins 156 may be used in accordance with the present invention. Additionally, the slots 150 need not be straight and aligned with the axis of the housing 140. The slots 150 may assume a slightly helical shape for example.

Figure 4:
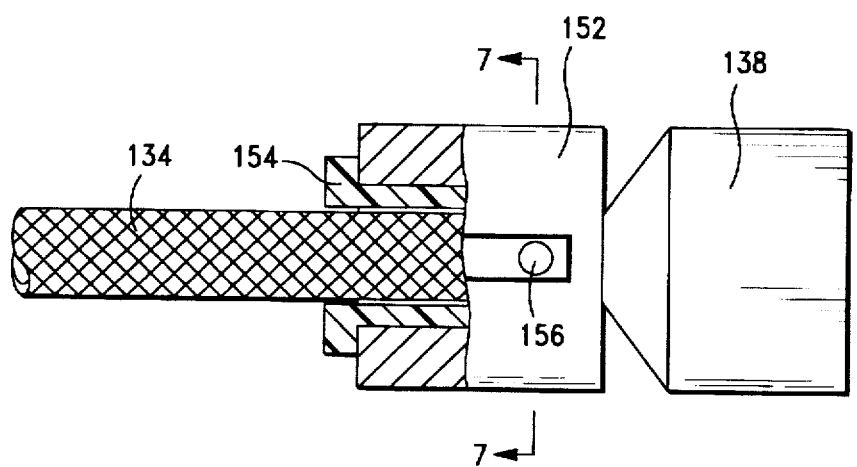
FIG. 4 is a partial cross-sectional view of the cutting blade and slider shown in FIG. 3.
Figure 5:
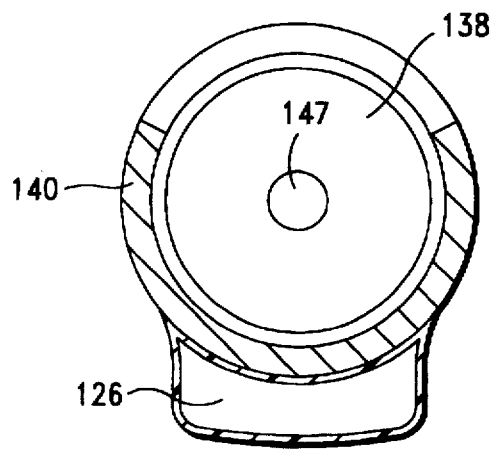
FIG. 5 is a cross-sectional view of FIG. 3 taken alone line 5—5 looking in the direction of the arrows.
Figure 6:
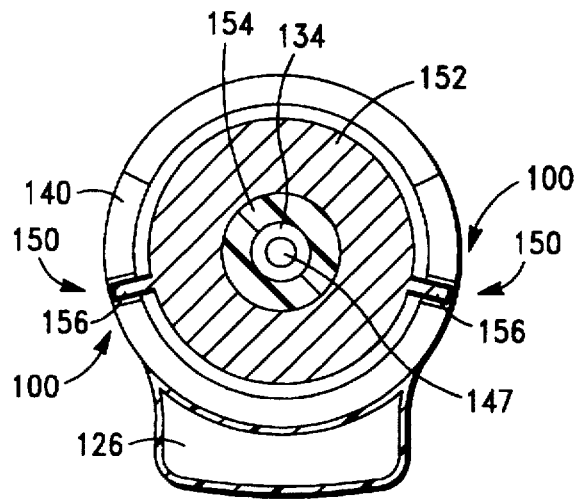
FIG. 6 is a cross-sectional view of FIG. 3 taken along line 6—6 looking in the direction of the arrows.
Figure 7:
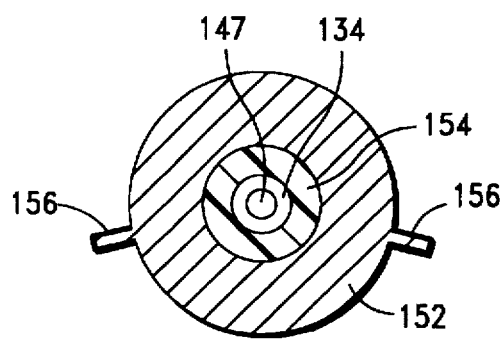
FIG. 7 is a cross-sectional view of FIG. 4 taken along line 7—7 looking in the direction of the arrows.

The pins 156 extend radially from the outer surface of the slider 152. The slider 152 is a cylinder and mounts over a bearing 154 (FIG. 4). The bearing 154 of the slider 152 mounts on the cable 134. When the cable 134 rotates, the slider 152 does not rotate. The slider 152 slides with the work element 138 and the cable 134.

The slider 152 is a cylinder mounted over a bearing 154 (FIG. 4). The bearing 154 mounts around cable 134. The interior of the bearing 154 is affixed to the cable 134 permitting the cable 134 and the interior of the bearing 154 to rotate (at high speed if necessary). The slider 152 remains rotationally stationary within the housing 140 when the cable 134 rotates. The bearing 154 maintains the position of the slider on the cutter torque cable.

The work element 138 is a cylindrical atherectomy cutting blade attached to the cable 134. Cable 134 rotation and translation respectively rotates or translates the work element 138. The slider 152 is also coupled to the cable 134 so that it will axially translate therewith. The slide 152 does not rotate when the cable 134 rotates. Thus, the slider 152 remains rotationally stationary with respect to the housing 140 even as the cable 134 rotates the work element 138. The slider 152 thus guides the work element 138 along the slots 150 with the pins 156.

The preferred embodiment illustrated in FIGS. 3–7 is useful with flexible housings and with rigid housings. Particular geometries and dimensions of the slots 150 and slider 152 and pins 156 may be varied widely within the scope of the present invention so long as the guiding structure 100 retains the work element 138 within the housing 140.

Figure 8:
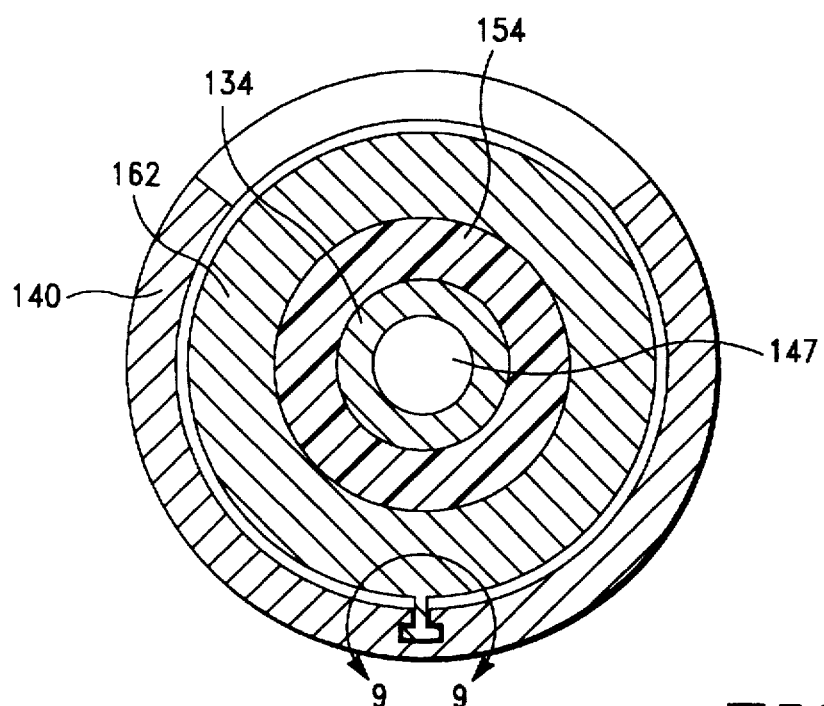
FIG. 8 is a cross-sectional view illustrating another embodiment of the guiding structure.
Figure 9:
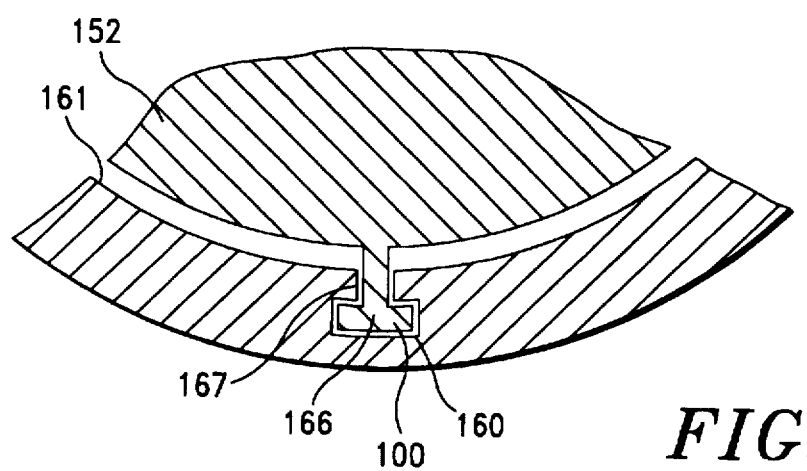
FIG. 9 is a partial sectional view of FIG. 8 taken along the line 9—9 looking in the direction of the arrows.

Referring now to FIGS. 8 and 9, a preferred embodiment of the pin 156 and the slots 150 of the atherectomy catheter 110 of FIG. 3 is shown. The pin 166 and the slot 160 shown in FIG. 8 differ in shape from the pins 156 and slots 150 of FIG. 6. A single pin and slot configuration is shown in FIG. 8 and FIG. 9. FIG. 8 shows a cross sectional view of the housing 140 of the present invention. FIG. 9 provides a larger scale view of the slot 160 and the pin 66 in the region demarcated by line 9—9 in FIG. 8.

The slot 160 is formed on the inner surface 161 of the housing 140. The pin 166 extends into the slot 160 partially through the housing 140. The pin 166 and the slot 160 may also extend fully through the housing 140 (see FIG. 3). As shown, the slot 160 tunnels longitudinally within the body of the housing 140. The slot 160 communicates with the hollow interior of the housing, 140 via a narrow-necked portion 167 of the slot 160. The pin 166 forms a "T" shaped cross-section that complements the shape of the narrow-necked portion 167 of the slot 160. The pin 166 is thus free to axially translate within the slot 160. The slot 60 radially locks the pin 166 with the housing 140. The slot 160 restrains the pin 66 an prevents movement of the pin 166 in the radial direction relative to the housing 140. A wide variety of pin/slot cross-sectional geometries (including, but not limited to a cross, a lollypop, an oblong, a diamond, etc.) provide the same functions of guidance and retention and are within the scope of the present invention. The pin 160 can also be a bar having the shape of a railroad track section for example.

Figure 10:
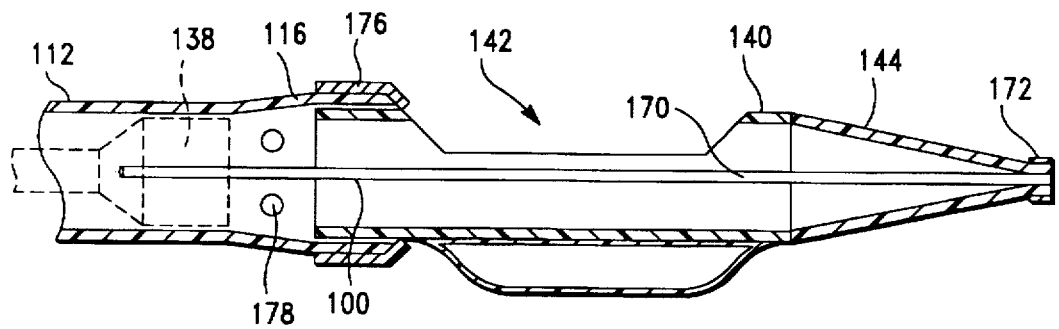
FIG. 10 is a cross-sectional side view of an additional embodiment of the guiding structure.
Figure 11:
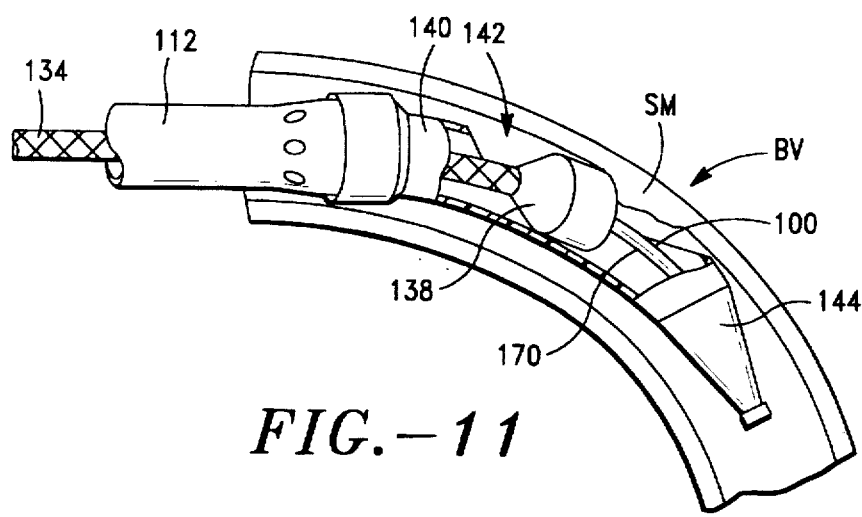
FIGS. 11 and 12 illustrate the operation of the atherectomy device of FIG. 10 in severing stenotic material from a blood vessel.
Figure 12:
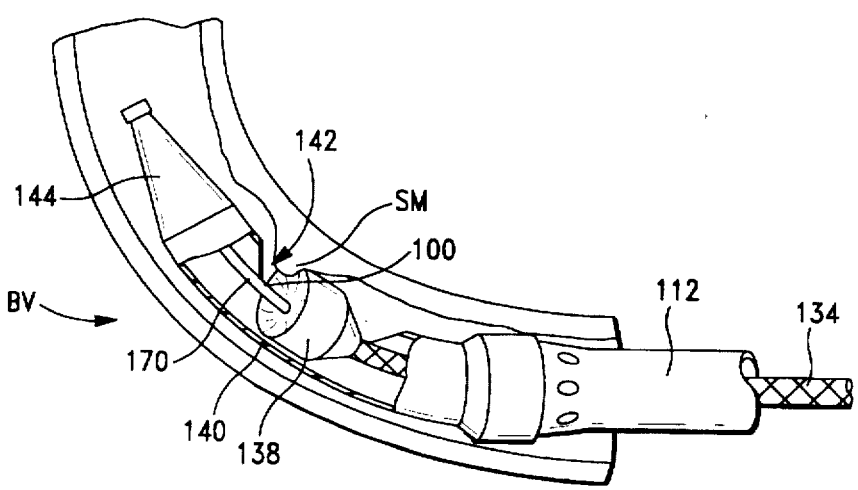

Referring now to FIGS. 10 through 12, another embodiment of the catheter of the present invention is shown. The invention includes housing 140 with window 142, catheter body 112, work element 138, cable 134, and coaxial rod or shaft 170. "BV" generaly indicates a cut away view of a blood vessel. "SM" indicates stenotic material on the interior wall of the blood vessel.

FIG. 10 is a cross-sectional side view of the housing 140. The guiding structure 100 includes a shaft 170. The shaft 170 attaches to the end 172 of the nose cone 144. The shaft 170 may be rigid or flexible, solid or hollow. Preferably, a flexible hollow shaft 170 is used with a flexible housing 140. As shown, the shaft 170 aligns coaxially with the housing 140 and is hollow for circumscribing a guidewire 146 (see FIG. 1). The housing is fabricated from a resilient material, such as an elastomeric polymer. The shaft 170 is formed from flexible material, for example, a tube formed from a superelastic alloy such as nickel-titanium alloy. A suitable superelastic alloy is commercially available and is fabricated under the trade name Nitinol® by Advanced Cardiovascular Systems, Santa Clara, Calif. Tubes formed from superelastic alloys desireably conform and bend in relation to the bending of the housing 140. Such tubes generally provide a smooth arc of curvature which the work element 138 follows.

Use of the shaft 170 guide system provides further advantages in that it facilitates proximal retraction of the work element 138, as illustrated in FIG. 10 in broken line. The work element 138 can be withdrawn proximally from the housing 140 into the catheter body 112 while the work element 138 remains on the shaft 170. The work element 138 is removed as an impediment to the flow of blood (or other fluid) from the interior of the distal portion of the catheter body 112 through the housing 140. The catheter body 112 is adapted to receive the work element 140 by flaring the distal end 116 of catheter body 112 over the proximal end of the housing 140, as illustrated. The distal end 116 can then be secured to the proximal end of the housing 140 using a connecting ring 76. Bypass perfusion ports 178 are provided within the distal portion of the catheter body 112 and proximal to the distal end of the catheter body 112, as described in more detail in copending application Ser. No. 08/236,485 filed Apr. 29, 1994 (attorney docket number DEVI 1464), and entitled "Catheter with Perfusion System", the full disclosure of which is incorporated herein by reference.

FIGS. 11 and 12 illustrate operation of an atherectomy catheter within the scope of the present embodiment. In FIG. 11 the housing 140 is located within a curved region of blood vessel BV. Stenotic material SM is located on the outer radius of the curve so that the housing 140 is located with housing window 142 directed radially outward. It will be appreciated that, with the housing 140 in such a configuration, the unguided work element 138 has a tendency to travel outward through the window 142 and into the wall of the blood vessel BV. Such a trajectory is not desirable since it can damage the blood vessel wall. Shaft 170 defines a curved travel path which maintains the work element 138 generally within the housing 140 and inhibits undesirable deviation of the cutter into the blood vessel wall.

Figure 13:
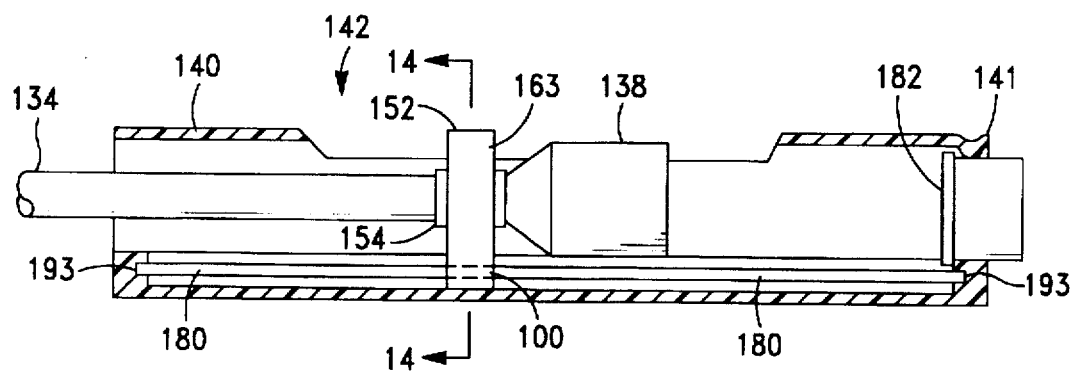
FIG. 13 is a cross-sectional view of a preferred embodiment of the guiding structure of the present invention.
Figure 14:
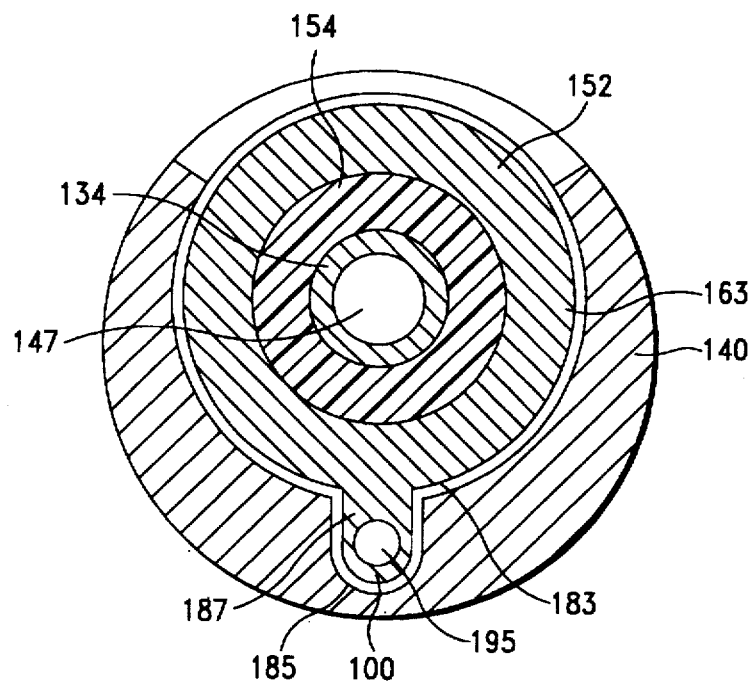
FIG. 14 is a cross-sectional view of FIG. 13 as seen along line 14—14 looking in the direction of the arrows.

In FIG. 12, use of an atherectomy catheter in removal of stenotic material SM along the inside radius of curvature of a blood vessel BV is illustrated. When the housing window 142 is on the inside radius of curvature, the work element 138 tends to cut into the inside wall of the housing 140, rather than cutting alone the optimal path for removal of stenotic material SM. The shaft 170 again defines the proper travel path for the work element 138 so that it avoids cutting into the housings 140 and is properly disposed to remove the stenotic material SM, as illustrated. Referring now to FIGS. 13 and 14, an embodiment of the catheter with a guiding structure 100 is illustrated. The embodiment includes housing 140 formed with a window 142, a work element 138, a cable 134, a ribbon 180, and a slider 152.

The housing includes a keyway 185. The work element 138 includes a slider 152 having an outer surface 163 with an extension 187. The extension 187 defines guide hole 195 which recieves the ribbon 180. The slider 152 holds the work element 138 in a desired position with respect to the housing 140.

The extension 187 slides along the keyway 185. The ribbon 180 holds the keyway 185 and the extension 187 together. The ribbon 180 extends from the proximal end 139 of the housing 140 to the distal end 141 of the housing 140. The holes 193 formed in the housing 140 hold each end of the ribbon 180. The ribbon 180 extends through the guide hole 195 formed in the housing 140 to lock the work element 138 against the housing 140.

FIG. 13 is a cross-sectional view of the housing FIG. 14 is a cross sectional view of the housing in FIG. 13 as seen along the line 14—14. The ribbon 180 is a shaft with a flat geometry and is secured to the distal end of housing 140, typically being attached to a ring 182 which secures the nose cone 144 to the housing. The ribbon 180 has a width that is at least 1.5 times its thickness, preferably at least 3 times its thickness. The ribbon 180 is metallic, and preferebly made from the family of metals known as superelastic alloys, and most preferably Nitinol®.

Referring now to FIGS. 15–18 still another embodiment of the catheter with guiding structure 100 is illustrated. The housing 140 has an outer surface 109 with a smooth exterior portion 191. The work element 138 is formed with an annular depression 192. The guiding structure 100 includes a band 190.

Figure 15:
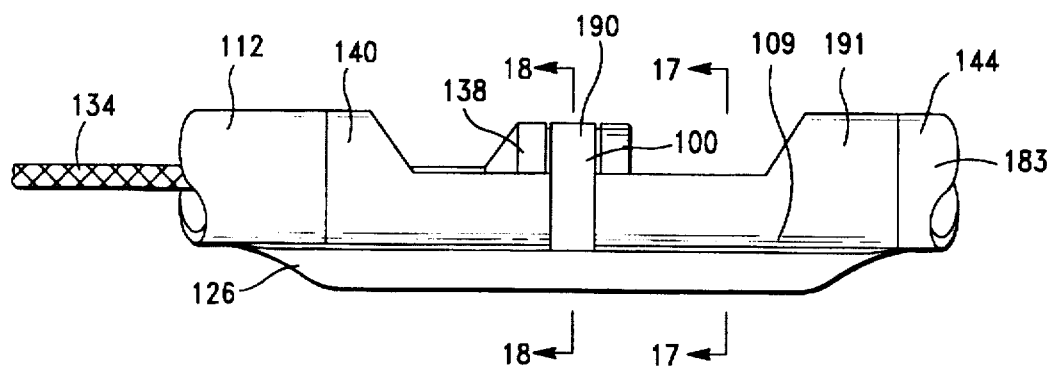
FIG. 15 is a side view illustrating a further embodiment of the guiding structure of the present invention.

FIG. 15 is a side view illustrating the outer surface 183 of the housing 140 and the guiding structure 100. The band 190 couples the work element 138 with outer surface 109 of the housing 140. An annular depression 192 forms in the housing 140. The annular depression 192 accepts the band 190. The band 190 surrounds the outer surface 109 of the housing 140 over the smooth portion 191 of the housing 140.

Figure 16:
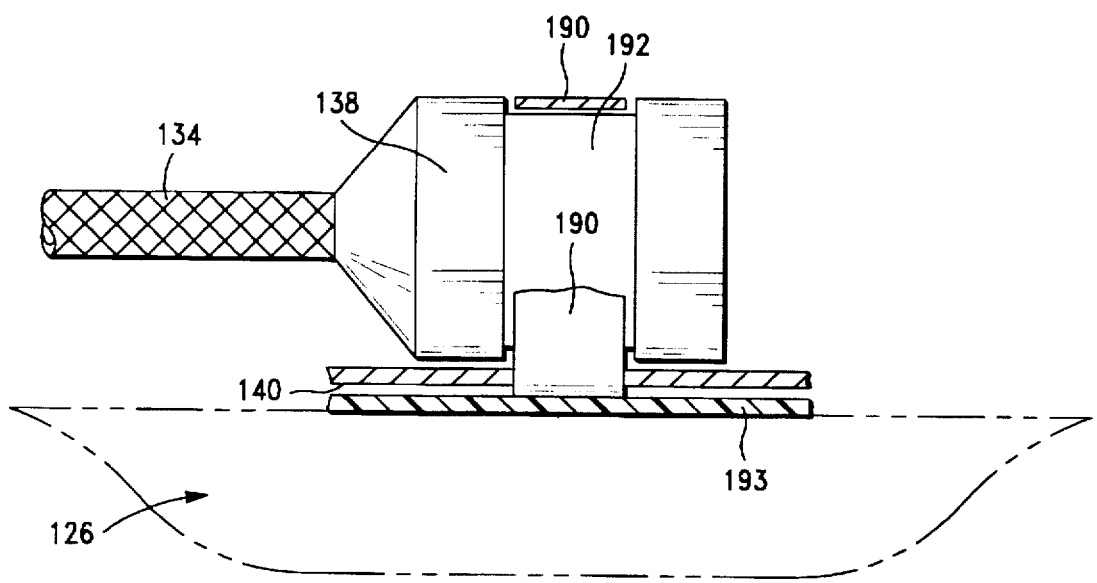
FIG. 16 is a side view illustrating a detail of the guiding structure shown in FIG. 15.

In FIG. 16, the work element attaches to a protective member 193. The annular depression 192, work element 138, protective member 193 and the band 190 are shown.

Figure 17:
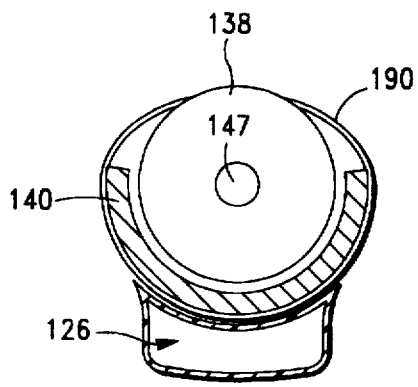
FIG. 17 is a cross-sectional view of FIG. 15 taken along line 17—17 looking in the direction of the arrows.
Figure 18:
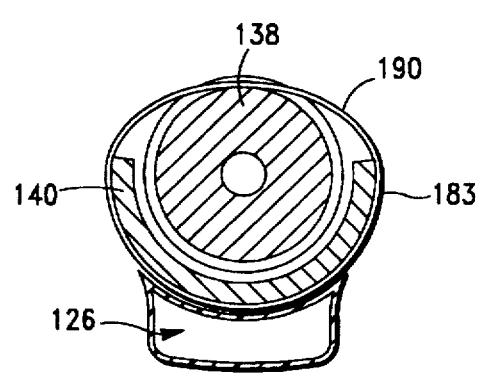
FIG. 18 is a cross-sectional view of FIG. 15 taken along line 18—18 looking in the direction of the arrows.

FIGS. 17 and 18 are cross-sectional views through the lines 17—17 and 18—18 respectively, shown in FIG. 15. The work element 138 rotates. The band 190 remains rotationally stationary. The band 190 flexes and translates axially when the work element 138 moves. The band 190 is fabricated from a metal, or a lubricious polymer, such as nylon, or polymers and copolymers of tetrafluoroethylene, or the like. The protective member 193 attaches to the housing 140 between the band 190 and the balloon 126 to prevent damage to the balloon 126 when the band 190 slides on the housing 140.

As described, the present invention is especially useful in atherectomy applications where the work element 138 is a rotating or rotationally oscillating cutting blade, and is operated by simultaneously rotationally translating and axially translating the blade 138 past the side window 142 in the housing 140 in order to sever and remove stenotic material from an area of interest, e.g. a stenosed region of blood vessel. However, other embodiments utilizing the guiding structures 100 described above are contemplated and are within the scope of the present invention. Examples of intravascular catheters containing alternative work elements 138 include, but are not limited to, cutting blades for performing atherectomy procedures, heated elements for performing thermal ablation, electrodes for performing electrosurgical cutting and cauterizing, abrasive elements for performing mechanical ablation, optical wave guides for performing laser ablation, ultrasonic transducers for imaging or ablation, fiber optical elements for visualization and imaging, and the like.

In each case, the cable 134 is appropriate to facilitate operation of the work element 138. For example, a cutting blade utilizes a cable, thermal ablators utilize electrical wires, laser ablators utilize optical elements, etc. Work element connectors appropriate for each work element are known to those skilled in the art.

It will be appreciated that intravascular introduction of a catheter, particularly into coronary arteries, frequently requires the catheter to pass through very tight turns and bends resulting from the tortuosity of the blood vessels. The guiding structure 100 of the present invention facilitates axial advancement of the cutting blade while the cutter housing is positioned in such tortuous regions, particularly by inhibiting loss of the cutting blade from flexible housings through the work window. The advantages of the present invention, however, also extend to the use of rigid cutter housings in less tortuous regions, where the cutter guide system of the present invention allows for the use of very wide work windows where, in the absence of the guide, the cutter would be at risk of escaping from the housing. Wider work windows are desirable for cutting, ablation, and viewing or imaging of larger regions of the vascular wall.

Fixed axial registration of the guiding member and housing help assure that the guiding member remains properly aligned within the housing. By "fixed", it is meant that the guiding member will not translate axially relative to the housing, although some degree of radial movement will be acceptable and, in some cases, even necessary. Axial paths defined by slots and channels which are formed in or on the interior surface of the housing will necessarily be fixed relative to the housing. Elongated members comprising shafts, bands and the like, are attached to the housing at least one end, preferably both ends. Such attachment may be direct, i.e., formed directly between the guiding member and a surface of the housing, or may be indirect, i.e., made through a separate component of the catheter which is itself fixed relative to the housing e.g., a nose cone, a housing connection ring, a portion of the catheter body, or the like. Such separately formed guiding members may, of course, directly or indirectly attach to the housing at more than one location.

Moveable guidewires have been used as a guiding structure in intravascular catheters. However, movable guidewires (which are free to axially translate relative to the housing) will often become axially misaligned within the housing as the catheter is advanced thereover. That is, the movable guidewire can be axially collapsed as the catheter is advanced, causing a pronounced lateral deflection within the interior of the housing. Such lateral deflection is unacceptable to define the axial path for the work element to track. The guiding structure 100s disclosed in the present invention solve this problem in that they define an axial path that is fixed relative to the housing.

Materials

As described, the housing may be rigid or flexible, typically being formed from a metal, such as surgical stainless steel, organic polymers such as polyacetyl, reinforced polymers such as graphite filled polyesters and ceramics. A rigid housing has a generally continuous construction, usually composed of a metal or rigid plastic, including the side window but free from other spacings or voids intended to enhance bendability. A flexible housing is usually formed from resilient materials, such as polyurethanes, elastomeric polyesters and the like, or if formed from metal or other rigid (non-resilient) material will include spacings or voids which are intended to facilitate bending. The constructions of particular flexible housings are illustrated in U.S. Pat. No. 4,781,186 and U.S. Pat. No. 5,226,909 the disclosures of which are incorporated herein by reference.

The slots formed in the housing may penetrate entirely through the housing wall, or may only partially penetrate the wall. A single slot may be formed, in which case it is desirable that the slot have cross-sectional geometry which locks in the coupling means, e.g., a T-shaped profile as illustrated in FIG. 8. In the case of multiple slots, it is less important that the coupling element be locked in. Coaxial shafts and off-set bands used as a guiding member may be rigid or flexible, depending primarily on the nature of the housing. Flexible tracking elements are preferred in flexible housings, but can also be used in rigid housings.

The elongated catheter body of the present invention typically comprises a flexible tube which can be similar in construction to a wide variety of intravascular catheters, the type which are well known in the art. The flexible tube will have a proximal end and a distal end and at least one lumen extending therebetween. The tube may be formed by extrusion of an organic polymer, typically a thermoplastic, such as nylon, polyurethane, polyethylene terephthalate (PET), polyvinylchloride (PVC), polyethylene, and the like. The tubes so formed may be reinforced or unreinforced, usually being reinforced by a metal braid which is laminated with the polymeric material. Use of the metal braid reinforcement layer is desirable since it facilitates torquing and positioning of the cutter housing, as described in more detail below. The catheter body will typically have a length from about 40 cm to 200 cm, with shorter catheters in the range from abut 40 cm to 120 cm being used for peripheral applications and longer catheters in the range from about 100 cm to 200 cm being used for coronary applications. The diameter of the catheter body may also vary, with smaller diameter catheters in the range from about 3 French (F; 1F=0.33 mm) to 6F, for coronary applications and a diameter from 3F to 11F for peripheral applications.

When the catheter is an atherectomy catheter, the cutter housing defines an open or hollow interior volume to receive stenotic material which penetrates or passes through the side window. The cutting blade is advanced past the window severing the stenotic material and advancing the severed atheroma toward the distal end of the housing. The distal end of the housing will typically be open and connected to a nose cone so that the severed stenotic material can be moved into the nose cone for storage.

In certain embodiments the cutter defines a cup-shaped cutting blade which is rotated (or rotationally oscillated) and advanced to sever the atheroma and urge the atheroma in a forward direction. Such cutting blades are illustrated in U.S. Pat. No. 4,979,951 and Reissue Pat. No. 33,569, the disclosures of which have previously been incorporated herein by reference.

The length of the cutter housing will depend primarily on the desired length of stenotic material to be severed, with the limitation that longer housings are more difficult to manipulate through the vascular system. Typically, the length of the housing is 5 mm to 40 mm. For coronary applications, the housing length will generally be at the shorter end of the range, usually being from about 8 mm to 17 mm. The housing diameter will generally correspond to the diameter of the flexible tube, i.e. usually being in the range from about 3F to 11F.

The cutter window within the housing typically extends over at least half of the housing length, and in other embodiments the cutter window extends over at least threequarters of the housing length. It will be appreciated that it is desirable to maximize the length of the housing in order to increase the amount of stenotic material which can be removed in a single pass of the cutting blade. It is also desirable to increase the width of the housing window for the same reason. The cutter guide system of the present invention is particularly advantageous since it permits cutter windows having a greater width that was generally possible with previous atherectomy catheter designs. For cylindrical housings, the cutter width will typically subtend an arc of at least 115°, preferably subtending an arc of at least 130°, and may subtend an arc of 180°, or greater. The use of such wide housing windows is possible only because the guide system of the present invention will contain the cutting blade generally within the interior of the housing, even when the housing is subjected to bending and other deformation stresses which might otherwise cause the cutter to escape from the housing through the housing window.

While the foregoing detailed description has described a preferred embodiment of the intravascular catheter, it is to be understood that the above description is illustrative only and not limiting of the disclosed invention. Particularly, the specific details of the geometry of slots and pins can differ from those illustrated and described so long as the guidance system guides and retains the work element within the housing. The invention is to be limited only by the claims set forth below.

What is claimed is:

1. An intravascular catheter for use in a blood vessel, comprising:

a catheter body having a proximal end, a distal end and a lumen therebetween;

a housing with a cylindrical body, a longitudinal axis, an internal surface, an external surface, a window on a lateral side thereof, and an open proximal end secured to the distal end of the catheter body, the housing defining a hollow interior;

a work element substantially disposed within the housing and having a proximal end;

a cable substantially disposed within the lumen of the catheter body, a connector having a proximal end and a distal end and the distal end being connected to the proximal end of the work element, the cable, connector and work element defining an interior tunnel surface;

a guiding structure disposed within the housing, the guiding structure having an outer surface, the outer surface defining a sliding length, the guiding structure being slidably connected to the work element, the sliding length and the interior tunnel surface defining at least one continuous sliding contact surface spanning the sliding length, whereby the work element is retained within the housing during insertion of the catheter within a blood vessel and during axial translation of the sliding contact surface within the housing.

2. An intravascular catheter for use in a blood vessel, comprising:

a catheter body having a proximal end, a distal end and a lumen therebetween;

a housing with a cylindrical body, a longitudinal axis, an internal surface, an external surface, a window on a lateral side thereof, and an open proximal end secured to the distal end of the catheter body, the housing defining a hollow interior and a slide surface, the slide surface having a length;

a work element substantially disposed within the housing and having a proximal end and a longitudinal axis;

a cable substantially disposed within the lumen of the catheter body, a connector having a proximal end and a distal end and the distal end being connected to the proximal end of the work element;

a guiding structure in slidable contact with the housing, the guiding structure being connected to the work element and completely encircling the longitudinal axis thereof, the guiding structure having a guide surface, the guide surface being in sliding contact with the housing slide surface, the guide surface and the housing slide surface defining at least one continuous, substantially straight, substantially longitudinally oriented contact surface spanning the length of the slide surface, whereby the work element is retained within the housing during insertion of the catheter within a blood vessel and during axial translation of the sliding contact surface within the housing.

3. An assembly for use with an intravascular catheter having a proximal end and a distal end and a cable, comprising:

a flexible housing, defining a substantially tubular surface, attachable to the distal end of the intravascular catheter, including a lateral window;

a work element, disposed within the housing and adjacent the lateral window, having a proximal end drivably connected to the cable of the intravascular catheter; and a guiding structure, having a rotatable, longitudinally fixed, laterally fixed attachment to the work element and having a rotationally fixed, laterally fixed, longitudinally slidable attachment to the housing, whereby, when the housing is bent within a tortuous blood vessel, the work element is constrained to advance and retreat within a volume substantially defined by the bent tubular surface of the housing.

4. The assembly of claim 3 wherein the housing includes an interior surface comprising at least one substantially longitudinal slot and the guiding structure includes a slider disposed about the cable proximate the proximal end of the work element, the slider comprising a surface defining an extension which extends into the slot in the interior surface of the housing.

5. The assembly of claim 4 wherein the slider comprises a bearing disposed about the cable and a cylinder disposed about the bearing.

6. The assembly of claim 3 wherein the housing includes an interior surface defining at least one substantially longitudinal slot having a profile relatively narrow at a depth near the juncture thereof with the interior surface of the housing and relatively broader at some depth between the narrow portion and the deepest portion of the slot; and the guiding structure includes a slider disposed about the cable proximate the proximal end of the work element, the slider including a surface defining a pin having a profile relatively narrow at a portion near the juncture thereof with the slider and relatively broader at a portion distal thereto, such that the distal portion of the pin extends into the broader portion of the slot and is retained therein by the relatively narrow portion of the slot;

the slider being held in longitudinally slidable and laterally restrained relation to the housing.

7. The assembly of claim 3 wherein the catheter body includes an inflation lumen, an inflatable balloon is disposed on the exterior surface of the housing opposite the lateral window, and the balloon fluidly communicates with the inflation lumen.

8. The assembly of claim 7 further comprising at least one perfusion port establishing a fluid path, from outside the assembly proximal to the balloon, to the housing interior, whereby perfusion of a blood vessel is achievable while the housing occupies the vessel lumen and the balloon is inflated.

9. The assembly of claim 3 wherein the housing includes a proximal end and a distal end each having an interior surface, and the guiding structure comprises:

at least one substantially longitudinal keyway formed in the interior surface of the housing;

at least one slider rotatably disposed about the cable proximate the proximal end of the work element, the slider comprising a lateral extension including a proximal surface, a distal surface, and at least one guide tunnel therebetween, the extension being slidably disposed in the keyway;

at least one shaft disposed in the keyway, having a proximal and distal end fixed in the interior surfaces of the proximal and distal ends, respectively, of the housing, the shaft passing through the guide tunnel of the slider to retain the extension in the keyway.

10. The assembly of claim 9 wherein the shaft is of flat ribbon geometry.

11. The assembly of claim 9 wherein the slider comprises a bearing disposed about the cable.

12. The assembly of claim 9 wherein the catheter body includes an inflation lumen, an inflatable balloon is disposed on the exterior surface of the housing opposite the lateral window, and the balloon fluidly communicates with the inflation lumen.

13. The assembly of claim 12 further comprising at least one perfusion port establishing a fluid path, from outside the assembly proximal to the balloon, to the housing interior, whereby perfusion of a blood vessel is achievable while the housing occupies the vessel lumen and the balloon is inflated.

14. An assembly for use with an intravascular catheter having a proximal end, a distal end, and a hollow drive cable including a distal end, comprising:

a flexible housing, defining a substantially tubular surface, attachable to the distal end of the intravascular catheter, including a lateral window, a distal end, and an interior surface;

a work element, disposed within the housing and adjacent the lateral window, including a proximal end drivably connected to the distal end of the hollow drive cable of the intravascular catheter, a distal end, and a tunnel between the proximal and distal ends communicating with the interior of the hollow drive cable; and a guiding structure, disposed within the housing, including a distal end attached to the interior surface of the distal end of the housing, also including a proximal end disposed through the tunnel of the work element and passable into the interior of the hollow drive cable; the guiding structure being in rotatable, longitudinally slidable, laterally fixed relation to the work element;

whereby, when the housing is bent within a tortuous blood vessel, the work element is constrained to advance and retreat within a volume substantially defined by the bent tubular surface of the housing.

15. The assembly of claim 14 wherein the guiding structure is attached to the center of the interior surface of the distal end of the housing.

16. The assembly of claim 14 wherein the guiding structure includes a hollow shaft capable of accommodating a guidewire.

17. The assembly of claim 14 wherein the guiding structure is resilient.

18. The assembly of claim 14 wherein the guiding structure is fabricated from a superelastic alloy.

19. The assembly of claim 14 wherein the guiding structure extends at least to the proximal end zone of the housing and is held substantially coaxial with the longitudinal axis of the housing in the proximal end zone thereof.

20. The assembly of claim 14 wherein an inflatable balloon is disposed on the exterior surface of the housing opposite the lateral window.

21. The assembly of claim 14 further comprising at least one perfusion port establishing a fluid path, from outside the assembly proximal to the balloon, to the housing interior, whereby perfusion of a blood vessel is achievable while the housing occupies the vessel lumen and the balloon is inflated.

22. An assembly for use with an intravascular catheter having a proximal end, a distal end, and a cable including a distal end, comprising:

a flexible housing, attachable to the distal end of the intravascular catheter, including a lateral window and defining a substantially tubular exterior surface;

a work element, disposed within the housing and adjacent the lateral window, including a distal end, a proximal end drivably connected to the distal end of the cable of the intravascular catheter, a cylindrical surface, and a depression circumscribing the cylindrical surface for receiving a circumferential band; and a guiding structure including a band slidably disposed about the exterior surface of the housing, a portion of the band being rotatably disposed about a portion of the depression circumscribing the cylindrical surface of the work element;

whereby, when the housing is bent within a tortuous blood vessel, the work element is constrained to advance and retreat within a volume substantially defined by the bent tubular surface of the housing.

23. The assembly of claim 22 wherein an inflatable balloon is disposed about the exterior surface of the housing on a side thereof opposite the lateral window.

24. The assembly of claim 23 wherein the housing includes a protective member disposed between the band and the balloon.

25. The assembly of claim 24 further comprising at least one perfusion port establishing a fluid path, from outside the assembly proximal to the balloon, to the housing interior, whereby perfusion of a blood vessel is achievable while the housing occupies the vessel lumen and the balloon is inflated.

26. The assembly of claim 23 wherein a protective member is disposed between the band and the balloon and is attached to the work element.

27. The assembly of claim 26 further comprising at least one perfusion port establishing a fluid path, from outside the assembly proximal to the balloon, to the housing interior, whereby perfusion of a blood vessel is achievable while the housing occupies the vessel lumen and the balloon is inflated.

* * * * *